(12) United States Patent
Kinoshiro et al.

(10) Patent No.: US 10,641,711 B2
(45) Date of Patent: May 5, 2020

(54) METHOD FOR ANALYZING NITROGEN IN METAL SAMPLE, APPARATUS FOR ANALYZING NITROGEN IN METAL SAMPLE, METHOD FOR ADJUSTING NITROGEN CONCENTRATION IN MOLTEN STEEL, AND METHOD FOR MANUFACTURING STEEL

(71) Applicant: JFE STEEL CORPORATION, Tokyo (JP)

(72) Inventors: Satoshi Kinoshiro, Kawasaki (JP); Masao Inose, Kawasaki (JP)

(73) Assignee: JFE STEEL CORPORATION, Tokyo (JP)

( * ) Notice: Subject to any disclaimer, the term of this patent is extended or adjusted under 35 U.S.C. 154(b) by 537 days.

(21) Appl. No.: 15/324,176

(22) PCT Filed: May 14, 2015

(86) PCT No.: PCT/JP2015/002447
§ 371 (c)(1),
(2) Date: Jan. 5, 2017

(87) PCT Pub. No.: WO2016/006147
PCT Pub. Date: Jan. 14, 2016

(65) Prior Publication Data
US 2017/0199129 A1    Jul. 13, 2017

(30) Foreign Application Priority Data

Jul. 9, 2014  (JP) .................................. 2014-141039
Jan. 20, 2015  (JP) .................................. 2015-008583

(51) Int. Cl.
*G01N 21/67* (2006.01)
*G01N 33/205* (2019.01)
(Continued)

(52) U.S. Cl.
CPC ............ *G01N 21/67* (2013.01); *B22D 11/001* (2013.01); *B22D 11/108* (2013.01); *B22D 11/11* (2013.01);
(Continued)

(58) Field of Classification Search
CPC ........ G01N 21/67; G01N 21/66; G01N 21/62; G01N 33/2025; G01N 33/2022; G01N 33/202; G01N 33/20
(Continued)

(56) References Cited

U.S. PATENT DOCUMENTS

| 5,522,915 A | 6/1996 | Ono et al. |
| 2007/0114002 A1 | 5/2007 | Blejde et al. |
| 2014/0011125 A1 | 1/2014 | Inoue et al. |

FOREIGN PATENT DOCUMENTS

| CN | 1286399 A | 3/2001 |
| CN | 1375692 A | 10/2002 |

(Continued)

OTHER PUBLICATIONS

Khater, Laser-induced breakdown spectroscopy for light elements detection in steel: State of the art, Spectrochimica Acta Part B, 2013, 81, pp. 1-10. (Year: 2013).*

(Continued)

*Primary Examiner* — Christine T Mui
(74) *Attorney, Agent, or Firm* — Ratnerprestia (57) ABSTRACT

Provided are a method for analyzing nitrogen in a metal sample, an apparatus for analyzing nitrogen in a metal sample, a method for adjusting nitrogen concentration in molten steel, and a method for manufacturing steel. The method includes: a melting process in which a metal sample containing a nitrogen component is melted in an argon gas atmosphere by performing impulse heating to gasify the nitrogen component; and an analyzing process in which (Continued)

nitrogen content in the metal sample is determined by analyzing nitrogen gas generated in the melting process and the argon gas by using a gas discharge optical emission method. By analyzing the nitrogen concentration of a sample taken from molten steel by using the analysis method described above, and by determining treatment conditions for adjusting nitrogen concentration on the basis of the nitrogen analysis value derived by the analysis, nitrogen concentration in molten steel is adjusted.

21 Claims, 4 Drawing Sheets

(51) Int. Cl.

| | | |
|---|---|---|
| *G01N 21/73* | (2006.01) | |
| *G01N 33/2025* | (2019.01) | |
| *B22D 11/00* | (2006.01) | |
| *B22D 11/108* | (2006.01) | |
| *B22D 11/11* | (2006.01) | |
| *B22D 11/16* | (2006.01) | |
| *C21C 7/10* | (2006.01) | |
| *C22C 38/00* | (2006.01) | |
| *C22C 38/02* | (2006.01) | |
| *C22C 38/04* | (2006.01) | |
| *G01N 33/00* | (2006.01) | |
| *G01N 33/20* | (2019.01) | |

(52) U.S. Cl.
CPC ............... *B22D 11/16* (2013.01); *C21C 7/10* (2013.01); *C22C 38/002* (2013.01); *C22C 38/02* (2013.01); *C22C 38/04* (2013.01); *G01N 21/73* (2013.01); *G01N 33/0036* (2013.01); *G01N 33/205* (2019.01); *G01N 33/2025* (2019.01)

(58) Field of Classification Search
USPC ........................................................ 436/106
See application file for complete search history.

(56) References Cited

FOREIGN PATENT DOCUMENTS

| | | |
|---|---|---|
| CN | 101105456 A | 1/2008 |
| JP | 6281580 | 10/1994 |
| JP | 0921767 A | 1/1997 |
| JP | 09152319 A | 6/1997 |
| JP | 10281996 | 10/1998 |
| JP | H11132954 A | 5/1999 |
| JP | 2000055794 | 2/2000 |
| JP | 2000310606 | 11/2000 |
| JP | 3160827 B2 | 4/2001 |
| JP | 2002039941 A | 2/2002 |
| JP | 2003139708 | 5/2003 |
| JP | 3613016 | 1/2005 |
| JP | 2011099770 | 5/2011 |
| JP | 2011227467 A | 11/2011 |
| JP | 4844087 | 12/2011 |
| JP | 2013224461 | 10/2013 |

OTHER PUBLICATIONS

Shen et al, Simultaneous determination of oxygen, nitrogen and hydrogen in metals by pulse heating and time of flight mass spectrometric method, Talanta, 2011, 84, 1057-1062. (Year: 2011).*
International Search Report and Written Opinion for International Application No. PCT/JP2015/002447, dated Aug. 4, 2015, 5 pages.
Taiwanese Office Action with partial English language translation for Application No. 104121645, dated May 13, 2016, 4 pages.
Hosmani, S.S., et al., "Nitrogen absorption by Fe-1.04at.%Cr alloy: uptake of excess nitrogen," Feb. 20, 2008, pp. 2618-2624, vol. 43(8), Journal of Materials Science.
Siafakas Kungliga, D., et al., "Investigation of hydrogen and nitrogen content in compacted graphite iron production—Master Thesis Project," Jan. 1, 2012, XP055328800, Retrieved from the Internet: URL:http://www.diva-portal.se/smash/get/diva2:606489/FULLTEXT01.pdf [retrieved on Dec. 13, 2016], 43 pages.
Extended European Search Report for European Application No. 15818600.7, dated Jun. 7, 2017, 15 pages.
Chinese Office Action for Chinese Application No. 201580037442. 6, dated Aug. 28, 2018 with Concise Statement of Relevance of Office Action, 5 pages.

* cited by examiner

METHOD FOR ANALYZING NITROGEN IN METAL SAMPLE, APPARATUS FOR ANALYZING NITROGEN IN METAL SAMPLE, METHOD FOR ADJUSTING NITROGEN CONCENTRATION IN MOLTEN STEEL, AND METHOD FOR MANUFACTURING STEEL

CROSS REFERENCE TO RELATED APPLICATIONS

This is the U.S. National Phase application of PCT International Application No. PCT/JP2015/002447, filed May 14, 2015, and claims priority to Japanese Patent Application No. 2014-141039, filed Jul. 9, 2014, and Japanese Patent Application No. 2015-008583, filed Jan. 20, 2015, the disclosures of each of these applications being incorporated herein by reference in their entireties for all purposes.

FIELD OF THE INVENTION

The present invention relates to a method for analyzing nitrogen in a metal sample, an apparatus for analyzing nitrogen in a metal sample, a method for adjusting nitrogen concentration in molten steel, and a method for manufacturing steel. The present invention relates to, in particular, an analysis method and an analysis apparatus which can preferably be used for determining nitrogen content in a metal sample such as steel or a titanium alloy, a method for adjusting nitrogen concentration in molten steel, and a method for manufacturing steel.

BACKGROUND OF THE INVENTION

In general, it is known that nitrogen included in metals such as titanium alloys and steel has various influences on the properties of the metals. Specifically, nitrogen is an interstitial solid-solution strengthening element and a chemical element which is effective for increasing strength by stabilizing the a phase of a titanium alloy and steel. On the other hand, it is known that nitrogen decreases the toughness of steel.

Therefore, for example, in the steel industry, the chemical composition of the products is adjusted on the basis of a nitrogen analysis value in the middle of a refining process in order to manufacture steel products having desired properties. Therefore, there is a demand for a method for rapidly determining nitrogen content in a metal sample with a high accuracy, as a method for analyzing nitrogen in metal, which can be used for adjusting a chemical composition in the middle of a refining process.

Conventionally known examples of a method for analyzing nitrogen in steel include wet methods such as a distillation-bispyrazolone spectrophotometric method and an inert gas fusion thermal conductivity detection method (Non Patent Literature 1). In particular, as a method for analyzing a nitrogen component in a steel-manufacturing process, an inert gas fusion thermal conductivity detection method is widely used from the viewpoint of analysis rapidness.

In addition, in the case of metals other than steel, it is known that wet analysis methods and an inert gas fusion thermal conductivity detection method are used (Non Patent Literatures 2 through 4).

An inert gas fusion thermal conductivity detection method is a method in which nitrogen content in a metal sample is determined by melting a metal sample in a graphite crucible in an inert gas stream (carrier gas) in an impulse furnace, by flowing nitrogen gas generated by the fusion of the sample into a thermal conductivity detector, and by determining the thermal conductivity of the carrier gas containing nitrogen gas.

In the case where an inert gas fusion thermal conductivity detection method is used, the following problems exist.

A gas generated from a metal sample is not limited to just nitrogen. For example, in the case of a steel sample, it is known that, when a steel sample is melted in an inert gas atmosphere in a graphite crucible, hydrogen gas and carbon monoxide gas are generated in addition to nitrogen gas, as disclosed in Patent Literature 1. These gases are generated as a result of hydrogen and oxygen contained in the steel sample gasifying or reacting with the graphite crucible to form gases. Such gases coexisting with nitrogen (hereinafter, referred to as "coexisting gases") decrease the accuracy of nitrogen content determination. In particular, carbon monoxide gas, which has a thermal conductivity close to that of nitrogen gas, causes a large analysis error in the case where it is not removed. Therefore, when nitrogen in a steel sample is analyzed, it is necessary to remove coexisting gases before transporting generated nitrogen gas to a thermal conductivity detector in order to determine the content of nitrogen gas. In order to remove coexisting gases, first, by passing gases generated from a melted steel sample through a column filled with oxidation catalyst, carbon monoxide gas and hydrogen gas are respectively oxidized into carbon dioxide and water vapor. Subsequently, generally, carbon dioxide gas is removed by passing the oxidized gases through a $CO_2$ remover composed mainly of sodium hydroxide, and then, water vapor is removed by passing the gases through a dehydrator composed mainly of magnesium perchlorate. By flowing the mixed gas of nitrogen gas and a carrier gas from which coexisting gases, which have a negative effect on analysis, have been removed to a thermal conductivity detector in order to determine thermal conductivity, nitrogen concentration in the steel sample is calculated from the relationship between the detected thermal conductivity and nitrogen concentration and the weight of the sample determined in advance. Here, since there is a decrease in the capability of reagents used in the oxidation column, the $CO_2$ remover, and the dehydrator described above due to determination being repeatedly performed on samples, the reagents are periodically replaced in order to maintain satisfactory analysis accuracy. However, in the case where a steel sample is analyzed in a practical steelmaking process, there is a case of an abnormal nitrogen analysis value even though the removal of the coexisting gases and the replacement of the reagents are rigorously practiced.

In addition, in the case where nitrogen analysis is performed by using an inert gas fusion thermal conductivity detection method, there is a problem in that it is necessary to use expensive helium gas as a carrier gas. In a thermal conductivity detection method, since the amount of change in thermal conductivity of gases is a signal value, the sensitivity of a detector increases with increasing difference in thermal conductivity between a carrier gas and an analysis target gas. Conversely, in the case of an analysis target gas having a thermal conductivity close to that of a carrier gas, since a change in thermal conductivity is small, detection is difficult. That is, in the case where nitrogen gas, which has a comparatively low thermal conductivity, is detected, helium, which has a high thermal conductivity, is the only carrier gas option available. Also, Non Patent Literatures 1 through 4 mentioned above state that helium should be used.

However, since helium is a gas whose abundance ratio in the air is very small, unlike argon, which is another kind of inert gas, producing helium by separating it from the air is not economically viable, and helium is produced by refining crude helium gas which is produced along with a natural gas. Therefore, helium gas is produced only in some particular countries, and there is a case where its supply is stopped depending on the political situation of the producing countries. In addition, nowadays, since there is a significantly growing demand for helium gas for use as a coolant or for medical purposes, the price of helium gas is very high, and a further price increase is anticipated. Therefore, an inert gas fusion thermal conductivity detection method, which requires the use of helium, is a method which incurs high cost and which has difficulty persisting.

Moreover, examples of a method for analyzing nitrogen in steel include spark atomic emission spectrometry, which is described in Non Patent Literature 5, Patent Literature 2, and Patent Literature 3. This method is a method in which, by inducing spark discharge on the surface of a steel sample for several seconds, and by determining light emitted when nitrogen atoms in an excited state generated from the surface of the sample return to the ground state, nitrogen concentration in the sample is derived, and this method is known to be excellent in terms of rapidness. However, there is a problem in that spark atomic emission spectrometry is poor in terms of the accuracy or precision of analysis values. This is, for example, because it is not easy to excite nitrogen so as to emit light, since nitrogen has a higher ionization energy than other chemical elements. In addition, since the analytical wavelength of nitrogen atoms is 149 nm, which is within the vacuum ultraviolet region, it is not easy to stably detect the light due to, for example, absorption by oxygen, significant attenuation by optical systems such as mirrors and lenses, and long-period attenuation caused by the degradation of the surfaces of optical systems over time. Although Patent Literature 2 and Patent Literature 3 mentioned above disclose techniques for solving such problems, since the absolute quantity of the steel sample to be determined is so small as to be less than 1 mg in the case of spark atomic emission spectrometry, the representativeness of the data is low, which results in fundamental limitations on the improvement of accuracy.

Here, nitrogen concentration in molten steel is analyzed by performing nitrogen analysis and adjusted in secondary refining processes including one in which a decarburization furnace is used and subsequent processes in which, for example, a RH vacuum degasser is used. Patent Literatures 4 through 6 discloses techniques in which target nitrogen concentration is achieved by analyzing nitrogen concentration in molten steel immediately before nitrogen-concentration adjustment is performed and by controlling a nitrogen-concentration-adjusting treatment on the basis of the analytical result. Usually, nitrogen concentration in molten steel is determined by charging a sample taken from the molten steel into an inert gas fusion thermal conductivity detection apparatus. However, as described above, there is a potential problem of obtaining an abnormal nitrogen analysis value with an inert gas fusion thermal conductivity detection method. For example, as Patent Literature 6 indicates, in the case where argon gas is circulated in an RH degasser immediately before an analysis sample is taken, since there is a case where the taken sample contains argon gas, a nitrogen analysis value higher than the practical value is derived if the portion containing argon gas is analyzed by using an inert gas fusion thermal conductivity detection method. It is needless to say that, in the case where a nitrogen analysis value is incorrect as described above, nitrogen concentration of finally obtained molten steel is different from a target nitrogen concentration.

PATENT LITERATURE

[PTL 1] Japanese Unexamined Patent Application Publication No. 2000-310606
[PTL 2] Japanese Unexamined Patent Application Publication No. 6-281580
[PTL 3] Japanese Unexamined Patent Application Publication No. 10-281996
[PTL 4] Japanese Patent No. 3613016
[PTL 5] Japanese Patent No. 4844087
[PTL 6] Japanese Unexamined Patent Application Publication No. 2013-224461

Non Patent Literature

[NPL 1] JIS G 1228
[NPL 2] JIS H 1612
[NPL 3] JIS H 1653
[NPL 4] JIS H 1685
[NPL 5] JIS G 1253

SUMMARY OF INVENTION

The present invention has been completed in view of the situation described above, and an object of the present invention is to provide a method for analyzing nitrogen in a metal sample with which nitrogen content in a metal sample is determined accurately and at low cost, an apparatus for analyzing nitrogen in a metal sample, a method for adjusting nitrogen concentration in molten steel, and a method for manufacturing steel.

Solution to Problem

The present inventors conducted investigations in order to solve the problems described above and obtained the following knowledge.

First, the reason for the decrease in accuracy of analysis values in the case of an inert gas fusion thermal conductivity detection method was closely investigated. As a result, only in the case of samples taken in some particular steel-making processes, a phenomenon in which there was a decrease in the accuracy of nitrogen analysis was observed. Specifically, there is a case where argon gas bubbling is performed in molten steel in a steel-making process, for example, in order to promote the stirring of molten steel, to promote the floatation of deoxidation products, and to perform denitrification, and it was found that there was a decrease in the accuracy of nitrogen analysis in the case of samples taken under such a condition. It is considered that such a decrease occurs by the following mechanism. That is, in the case where argon gas blown into molten steel is trapped in a taken sample, and in the case where such a sample is subjected to analysis by using an inert gas fusion thermal conductivity detection method, argon gas having a low thermal conductivity is generated along with nitrogen gas and coexisting gases. It is considered that, since such argon gas reaches a thermal conductivity detector without being removed, an abnormal analysis value is derived. Therefore, investigations regarding a method for removing argon gas, as with coexisting gases, were conducted. However, no effective removing method was found, because, for example, argon gas is an inert gas.

Therefore, the present inventors considered whether it is possible to solve the problem of generated argon gas by using argon gas as a carrier gas. Although argon gas can preferably be used to melt a steel sample because argon gas is an inert gas as is the case with helium gas, as described above, since the thermal conductivity of argon gas is almost equal to that of nitrogen gas, which is the analysis target gas, it is not possible to detect argon gas by using a thermal conductivity detecting method. Therefore, the present inventors conducted investigations regarding other methods for detecting nitrogen and conceived a method for detecting nitrogen by utilizing discharge optical emission in a gas. That is, by melting a metal sample containing a nitrogen component in an argon gas atmosphere by performing impulse heating in order to gasify the nitrogen component, and by then analyzing argon gas containing nitrogen generated as a result of melting the metal sample by using a discharge optical emission method, nitrogen content in the metal sample is determined. It was found that, with this, it is possible to determine nitrogen content in a metal sample accurately and at low cost.

It is possible to render the negative effect of argon gas generated from a metal sample harmless by using argon gas as a carrier gas and by analyzing nitrogen by using a gas discharge optical emission method. Moreover, it is possible to eliminate a problem of high cost and sourcing difficulty caused by the use of helium gas.

The present invention has been completed on the basis of the knowledge described above and is characterized as follows.

[1] A method for analyzing nitrogen in a metal sample, the method including: a melting process in which a metal sample containing a nitrogen component is melted in an argon gas atmosphere by performing impulse heating to gasify the nitrogen component, and an analyzing process in which nitrogen content in the metal sample is determined by analyzing nitrogen gas generated in the melting process and the argon gas by using a gas discharge optical emission method.

[2] The method for analyzing nitrogen in a metal sample according to item [1] above, in which, when nitrogen content is determined by using the gas discharge optical emission method, optical emission at one or more of wavelengths 337 nm, 357 nm, 380 nm, and 406 nm of nitrogen gas are used.

[3] The method for analyzing nitrogen in a metal sample according to item [1] or [2] above, in which, when nitrogen content is determined by using the gas discharge optical emission method, emission intensity of nitrogen gas is corrected in accordance with emission intensity of argon gas that is determined at the same time as determining the emission intensity of nitrogen gas or when not determining the emission intensity of nitrogen gas with flowing only argon gas.

[4] The method for analyzing nitrogen in a metal sample according to item [3] above, in which, when nitrogen content is determined by using the gas discharge optical emission method, optical emission at one or more of wavelengths 697 nm, 727 nm, 751 nm, 764 nm, 772 nm, 795 nm, 801 nm, 812 nm, and 826 nm of argon gas are used.

[5] An apparatus for analyzing nitrogen in a metal sample, the apparatus including: an impulse furnace in which a metal sample containing a nitrogen component is melted in an argon gas atmosphere to gasify the nitrogen component; an argon gas feeding system through which argon gas is fed into the impulse furnace; a discharge optical emission system that induces the discharge optical emission of nitrogen gas generated in the impulse furnace and argon gas in the impulse furnace by using a gas discharge optical emission method; and a photometrical analysis system that determines the intensity of emission induced by the discharge optical emission system to determine nitrogen content in the metal sample.

[6] The apparatus for analyzing nitrogen in a metal sample according to item [5] above, in which the photometrical analysis system further includes a device that determines emission intensity of the argon gas.

[7] The apparatus for analyzing nitrogen in a metal sample according to item [5] or [6] above, the apparatus further including a carbon dioxide measuring device of an infrared absorption type for determining carbon dioxide content between the impulse furnace and the discharge optical emission system.

[8] The apparatus for analyzing nitrogen in a metal sample according to any one of items [5] to [7] above, the apparatus further including a buffer for diluting the nitrogen component in the argon gas between the impulse furnace and the discharge optical emission system.

[9] The method for analyzing nitrogen in a metal sample according to any one of items [1] to [4] above, in which, when the nitrogen component is gasified by the impulse heating, the metal sample containing a nitrogen component is heated to a temperature of 2500° C. or higher.

[10] A method for adjusting nitrogen concentration in molten steel, the method including: taking a sample from molten steel; analyzing the nitrogen concentration of the taken sample by using the method for analyzing nitrogen in a metal sample according to any one of items [1] to [4] and [9] above; and determining treatment conditions for adjusting nitrogen concentration on the basis of the nitrogen analysis value obtained through the analyzing.

[11] A method for manufacturing steel, the method including manufacturing steel by performing continuous casting on molten steel whose nitrogen concentration has been adjusted by using the method for adjusting nitrogen concentration in molten steel according to item [10] above.

Advantageous Effects of Invention

By using the analysis method and the analysis apparatus according to the present invention, it is possible to determine nitrogen content in a metal sample accurately and at low cost. In addition, by analyzing nitrogen concentration by using the analysis method according to the present invention in a process for adjusting nitrogen concentration in molten steel included in a steel-making process, it is possible to securely achieve the target value of nitrogen concentration in a steel product.

DETAILED DESCRIPTION OF EMBODIMENTS OF THE INVENTION

Hereafter, the method for analyzing nitrogen in a metal sample according to the present invention will be described in detail by using the apparatus for analyzing nitrogen in a metal sample according to the present invention.

Figure 1:
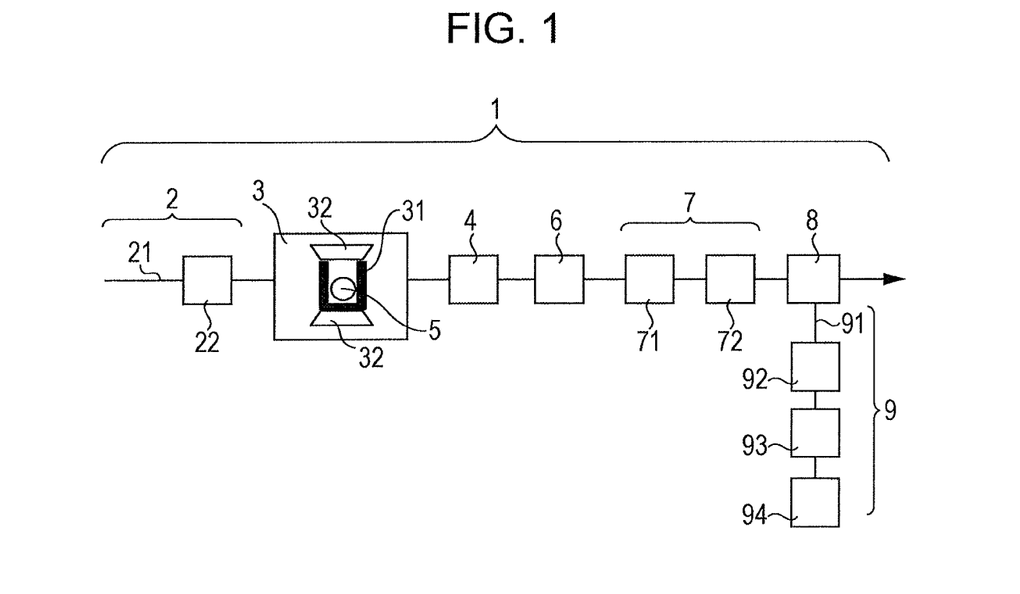
FIG. 1 is a diagram illustrating the apparatus for analyzing nitrogen in a metal sample according to the present invention.

FIG. 1 is a diagram illustrating one example of the apparatus for analyzing nitrogen in a metal sample according to the present invention. In FIG. 1, an apparatus for analyzing nitrogen 1 has an argon gas feeding system 2, an impulse furnace 3 in which a metal sample 5 is melted in an atmosphere containing the argon gas fed through the argon gas feeding system 2 in order to gasify a nitrogen component contained in the metal sample 5, a dust filter 4 which removes dust which has been generated due to the melting of the metal sample 5 in the impulse furnace 3, an oxidation column 6 in which hydrogen gas and carbon monoxide gas in a mixed gas containing mainly argon from which dust has been removed are respectively oxidized into water vapor and carbon dioxide, a column system 7 which removes the water vapor and the carbon dioxide from the mixed gas containing mainly argon gas, a discharge optical emission system 8 which induces discharge optical emission in the nitrogen-containing argon gas from which water vapor and carbon dioxide have been removed, and a photometrical analysis system 9 which determines the light emitted from the discharge optical emission system 8 in order to determine nitrogen content in the metal sample. Examples of a metal sample which is analyzed by the apparatus for analyzing nitrogen 1 include a sample composed of a titanium alloy and a sample composed of steel.

Moreover, the argon gas feeding system 2 has an argon gas source (not illustrated), an argon gas feeding line 21, and a flow rate adjuster 22, which is a flow rate controller placed on the argon gas feeding line 21.

In the impulse furnace 3, a graphite crucible 31, in which the metal sample 5 is contained, and electrodes 32, which hold the graphite crucible 31, are placed, and the electrodes 32 are connected to a power supply (not illustrated). In addition, in this impulse furnace 3, by applying an alternating current of, for example, 700 A to the electrodes 32 in an atmosphere containing argon gas fed through the argon gas feeding system 2, the metal sample 5 in the graphite crucible 31 is rapidly melted, and a nitrogen component, a hydrogen component, an oxygen component, and an argon component which have been contained in the metal sample 5 are respectively gasified into nitrogen gas, hydrogen gas, carbon monoxide, and argon gas.

In order to protect the discharge optical emission system 8 placed downstream, the dust filter 4 is intended to remove dust generated from the metal sample 5 and the graphite crucible 31 from the mixed gas containing mainly argon (nitrogen-containing argon gas) which has been generated in the impulse furnace 3, and the dust filter 4 is placed as needed between the impulse furnace 3 and the oxidation column 6. Examples of the dust filter 4 include a filter excellent in terms of gas permeability which is composed of a silica fiber or polytetrafluoroethylene.

The oxidation column 6 is intended to respectively oxidize hydrogen gas and carbon monoxide gas generated from the metal sample 5 into water vapor and carbon dioxide gas and is placed as needed upstream of the column system 7. For this oxidation column 6, for example, copper oxide may be used.

The column system 7 has a $CO_2$ remover 71 and a dehydrator 72, which are respectively intended to remove carbon dioxide and wader vapor in the mixed gas, and is placed as needed upstream of the discharge optical emission system 8. Examples of the reagent of the $CO_2$ remover 71 include sodium hydroxide powder, and examples of the reagent of the dehydrator 72 include magnesium perchlorate powder.

The discharge optical emission system 8 is intended to induce discharge in the nitrogen-containing argon gas by applying an alternating voltage between a pair of electrodes while the nitrogen-containing argon gas from which carbon dioxide and water vapor have been removed is flowed between the pair of electrodes arranged at a certain distance. Examples of the structural material of the discharge optical emission system 8 include a material having a high optical transparency such as silica glass, and examples of the material of the electrodes include an electrolytic solution and metal. That is, a gas-discharge device or a silent-discharge-type ozone generator which is conventionally known and which has such a structure may be used.

The photometrical analysis system 9 has an optical fiber 91 which guides the light (having a wavelength of, for example, 337 nm) omitted when the nitrogen gas which has been exited by discharge induced by the discharge optical emission system 8 returns from the excited state to the ground state to a spectroscopic unit 92; the spectroscopic unit 92 which extract the emission wavelengths of nitrogen gas and the emission wavelengths of argon gas; a photometric unit 93 which determines the emission intensities corresponding to the emission wavelengths extracted by the spectroscopic unit 92; and an operation unit 94 which calculates nitrogen concentration in steel from the emission intensities derived by the photometric unit 93. Here, it is not always necessary to use the optical fiber 91 between the discharge optical emission system 8 and the spectroscopic unit 92, and light induced by the discharge optical emission system 8 may be directly led to the spectroscopic unit 92. Examples of the spectroscopic unit 92 include an optical filter such as a band-pass filter and a spectrometer utilizing diffraction gating. Examples of the photometric unit 93 includes a light-receiving device such as a photomultiplier tube, a CCD (Charge-Coupled Device), and a photodiode. The operation unit 94 calculates nitrogen concentration in the metal sample from the integrated emission intensities derived by the photometric unit 93 and the weight of the sample which has been determined in advance.

In addition, by using the apparatus in FIG. 1, it is possible to perform quantitative analysis on nitrogen contained in the metal sample 5 through, for example, the following procedures.

First, the metal sample 5 is charged into the graphite crucible 31. Argon gas is continuously fed into the impulse furnace 3 through the argon gas feeding system 2. In the impulse furnace 3, by applying a current to the electrodes 32, the metal sample 5 is melted in an argon gas atmosphere. Subsequently, a mixed gas containing mainly nitrogen-containing argon gas generated by the melting of the metal sample 5 is transported to the dust filter 4 in order to remove dust by using the dust filter 4, and, then, hydrogen and carbon monoxide are removed by using the oxidation column 6 and the column system 7. Subsequently, in the discharge optical emission system 8, by applying an alternating voltage to the pair of electrodes while the nitrogen-containing argon gas from which carbon dioxide and water vapor have been removed is flowed, discharge is induced in the nitrogen-containing gas. Subsequently, by analyzing the emitted light by using the photometrical analysis system 9, nitrogen concentration in the metal sample is determined from the amount of nitrogen gas generated by the melting of the metal sample 5.

With the procedures described above, since nitrogen gas generated by the melting of the metal sample 5 is transported with argon gas and analyzed by using a discharge optical emission method, it is possible to neglect the negative effect of argon gas generated from the metal sample 5, and it is possible to perform analysis at lower cost compared with in the case of the conventional technique in which nitrogen gas is transported with helium gas. In addition, a concern about gas supply stop is eliminated.

In the procedures described above, it is preferable to correct the emission intensity of nitrogen gas in accordance with the emission intensity of argon gas determined at the same time. In the discharge optical emission system 8, there is a case of a decrease in the optical transparency due to the stain of the silica member caused by the repetition of discharge. In such a case, since there is a decrease in emission intensity determined by the photometrical analysis system 9, a nitrogen analysis value determined by the photometrical analysis system 9 appears to be small. In response to such a problem, by adding a device that determines the emission intensity of argon gas to the photometrical analysis system 9 in order to determine the emission intensity of argon gas, by dividing the emission intensity of nitrogen gas by the emission intensity of argon gas in order to normalize the emission intensity of nitrogen gas, and by correcting the emission intensity of nitrogen gas in accordance with the emission intensity of argon gas every determination time or intermittently, it is possible to compensate for a decrease in intensity due to the stain of the silica glass, and it is possible to stably obtain a nitrogen analysis value. That is, it is possible to correct the emission intensity of nitrogen gas so that it is possible to eliminate the influence of a change in the emission intensity of nitrogen gas due to the stain of the discharge tube.

In addition, in the procedures described above, when the nitrogen component is gasified by performing impulse heating, it is preferable that the metal sample containing the nitrogen component be heated to a temperature of 2500° C. or higher.

Figure 2:
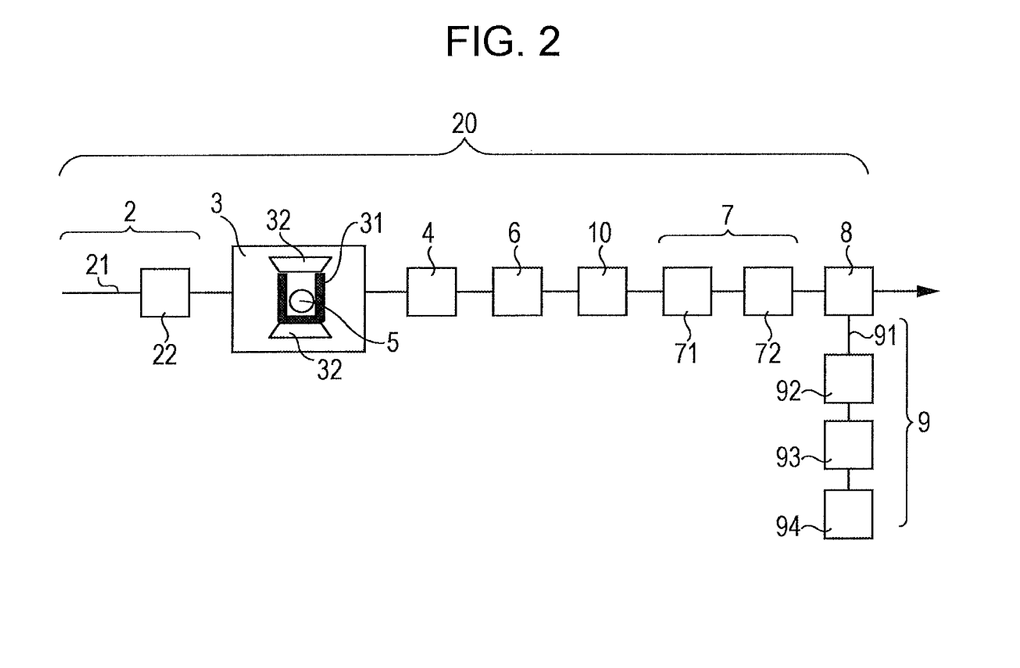
FIG. 2 is a diagram illustrating another kind of the apparatus for analyzing nitrogen in a metal sample according to the present invention.

Here, the analysis apparatus according to the present invention is not limited to the example described above and may be appropriately modified. For example, in the analysis apparatus according to the present invention, an infrared absorption type carbon dioxide measuring device 10 may further be placed downstream of the oxidation column 6, that is, between the oxidation column 6 and the column system 7 (FIG. 2: another kind of the apparatus 20 for analyzing nitrogen in a metal sample according to the present invention). Oxygen in a melted metal sample reacts with graphite crucible to form carbon monoxide, and such carbon monoxide is oxidized into carbon dioxide. By determining the content of such carbon dioxide by using the infrared absorption type carbon dioxide measuring device 10, it is possible to determine oxygen concentration in the metal sample in addition to nitrogen concentration at the same time. Examples of the infrared absorption type carbon dioxide measuring device 10 include an apparatus with which carbon dioxide concentration is determined on the basis of the amount of infrared having the natural wavelength of carbon dioxide absorbed.

Figure 6:
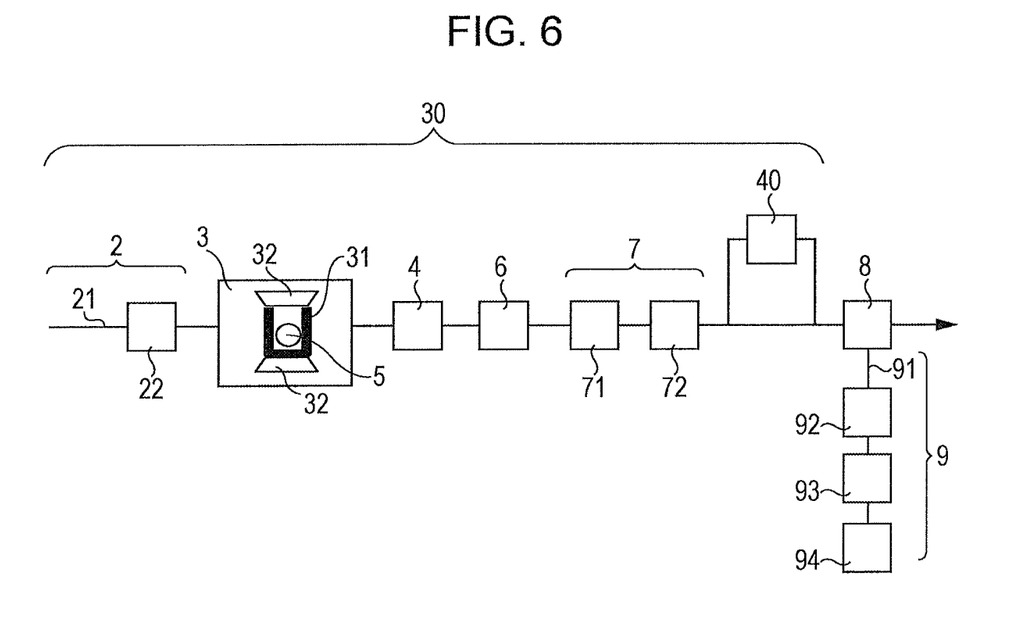
FIG. 6 is a diagram illustrating another kind of the apparatus for analyzing nitrogen in a metal sample according to the present invention.

Moreover, as an example of the embodiments of another kind of the apparatus for analyzing nitrogen in a metal sample according to the present invention, a buffer 40 may further be added between the column system 7 and the discharge optical emission system 8 (FIG. 6: another kind of the apparatus 30 for analyzing nitrogen in a metal sample according to the present invention). In the case where the nitrogen content of the metal sample 5 is high, since nitrogen concentration in argon gas is also high, there is a case where, since nitrogen molecules are insufficiently exited in the discharge optical emission system 8, low analysis value is derived. In contrast, by adding the buffer 40, argon gas having a high nitrogen concentration generated in the metal sample 5 is led to the discharge optical emission system 8 through the buffer 40. By flowing the argon gas through the buffer 40, since the highly concentrated nitrogen gas is diluted, it is possible to derive an accurate analysis value. In order to choose whether or not to flow the argon gas through the buffer 40 in accordance with nitrogen concentration, for example, it is preferable that the buffer 40 have a path-switching system in a pipe line. The buffer 40 has a vessel-type structure which has a sufficiently large cross section compared with the pipe line and which is filled with argon gas. When a gas to be analyzed containing highly concentrated nitrogen gas flows into the buffer 40, since the gas to be analyzed is diluted with the argon gas filled therein, there is the effect of decreasing nitrogen concentration in the gas to be analyzed which is led to the discharge optical emission system 8.

Figure 3:
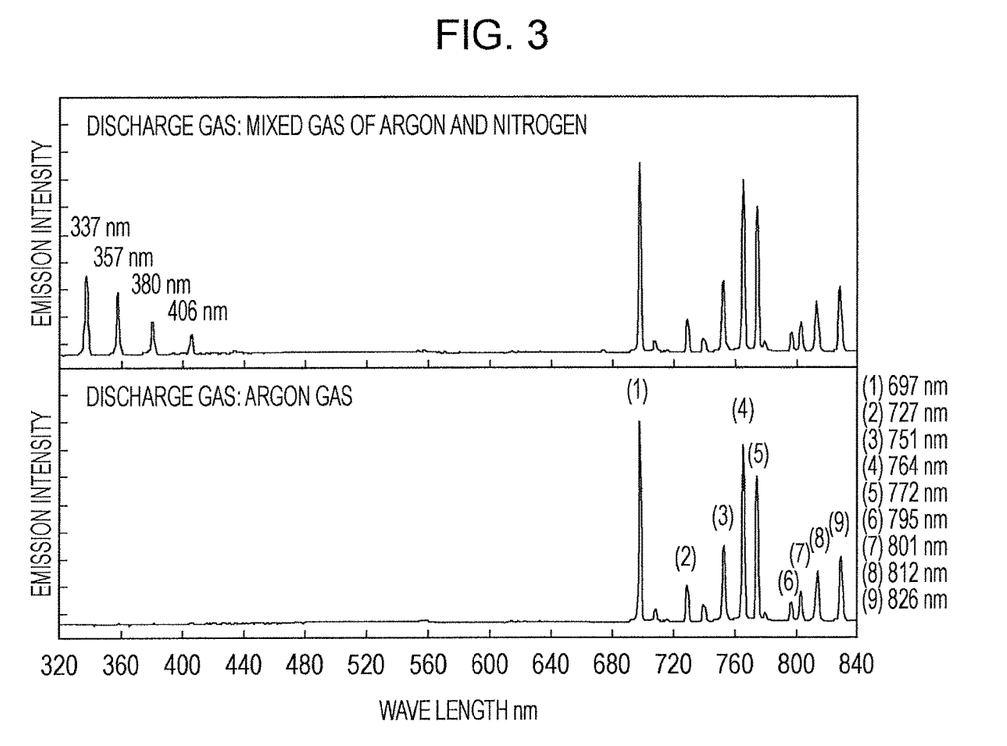
FIG. 3 is a diagram illustrating emission intensity in each of the cases where discharge occurs in a mixed gas of argon gas and nitrogen gas and where discharge occurs in argon gas.
Figure 4:
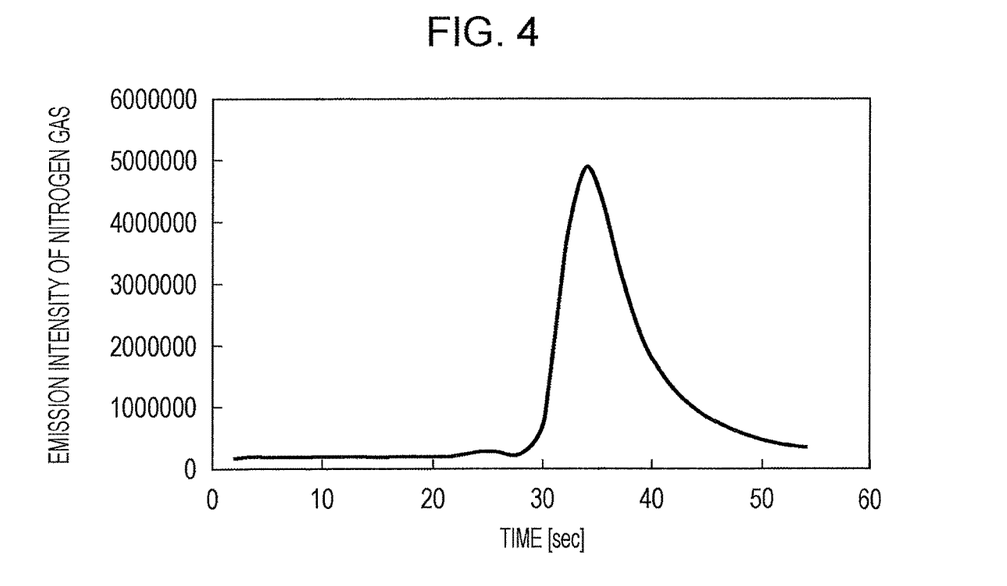
FIG. 4 is a diagram illustrating the determination result of a change over time in emission intensity at wavelength 337 nm when a steel sample is melted in an argon gas stream and discharge occurs in the argon gas.

FIG. 3 is a diagram illustrating emission intensity determined by using the photometrical analysis system 9 in the case where discharge was induced by flowing a mixed gas of argon gas and nitrogen gas or argon gas through the discharge optical emission system 8. As FIG. 3 indicates, as the emission wavelengths of nitrogen gas, wavelengths 337 nm, 357 nm, 380 nm, and 406 nm were observed, and, as the emission wavelengths of argon gas, wavelengths 697 nm, 727 nm, 751 nm, 764 nm, 772 nm, 795 nm, 801 nm, 812 nm, and 826 nm were observed. In addition, FIG. 4 is a diagram illustrating the determination result of a change over time in emission intensity at emission wavelength 337 nm when a steel sample was melted in an argon gas stream and discharge occurred in the argon gas. As FIG. 4 indicates, although the emission intensity at wavelength 337 nm changes over time, by reading an integrated value for a certain time (for example, 20 seconds from 30 seconds to 50 seconds after determination has been started), it is possible to achieve sufficient nitrogen-detection sensitivity. Therefore, by determining the emission intensity of nitrogen gas at any one of wavelengths 337 nm, 357 nm, 380 nm, and 406 nm, by converting an integrated value for a certain time into nitrogen amount in accordance with the standard curve, and by dividing the amount of nitrogen by the corresponding sample weight, it is possible to derive nitrogen concentration in the steel sample. In addition, by determining the emission intensity of argon gas at any one of wavelengths 697 nm, 727 nm, 751 nm, 764 nm, 772 nm, 795 nm, 801 nm, and 812 nm, by deriving an integrated value for a certain time as is the case with nitrogen, and by dividing the integrated value of the emission intensity of nitrogen gas described above by the derived integrated value in order to compensate for a decrease in the emission intensity of nitrogen gas due to the stain of a discharge cell, it is possible to stably derive nitrogen analysis value over a long period.

As described above, in the present invention, a discharge optical emission method is used as a method for analyzing nitrogen gas in argon gas. By using a discharge optical emission method, it is possible to detect nitrogen gas generated from a metal sample melted in argon gas with a high sensitivity without the negative effect of argon existing in the metal sample.

Here, examples of an apparatus combining the argon gas feeding system 2 and the impulse furnace 3 include a hydrogen analyzer which is usually placed in an analysis laboratory in a steel plant. By connecting the discharge optical emission system 8, the photometrical analysis system 9, and, as needed, the buffer 40 to the gas outlet port of the hydrogen analyzer, it is possible to perform desired analysis on nitrogen. In this case, however, it is necessary that the heating temperature of the impulse furnace be 2500° C. or higher. That is because nitrogen in steel is not gasified at a standard heating temperature (about 2000° C.) for analyzing hydrogen in steel. By controlling the heating temperature to be 2500° C. or higher, it is possible to solve a problem with the use of a hydrogen analyzer for hydrogen in steel in that nitrogen in steel is not gasified. In addition, for example, by performing two-step heating at temperatures of 2000° C. and 3000° C., it is also possible to analyze hydrogen and nitrogen in steel of one sample at the same time.

Moreover, by using the method for analyzing nitrogen in a metal sample according to the present invention, it is possible to adjust nitrogen concentration in molten steel in a steel-making process.

For example, a metal sample is taken at an appropriately selected time (for example immediately before nitrogen concentration is adjusted) in a steel-making process (refining process). Subsequently, the nitrogen concentration of the taken sample is analyzed by using the method for analyzing nitrogen in a metal sample according to the present invention. Subsequently, by determining the conditions of a steel-making process, in particular, the conditions of a treatment for adjusting nitrogen concentration in steel on the basis of the nitrogen analysis value obtained by the analysis, nitrogen concentration in molten steel in a steel-making process is adjusted. There is no particular limitation on what method is used for adjusting nitrogen concentration in molten steel. For example, a vacuum degassing apparatus such as an RH vacuum degasser may be used. As a result, it is possible to securely achieve a target value of nitrogen concentration in a steel product.

Moreover, it is possible to manufacture steel by performing continuous casting on molten steel whose nitrogen concentration has been adjusted by using the method for adjusting nitrogen concentration in molten steel according to the present invention.

For example, hot metal which has been tapped from a blast furnace is passed through a pretreatment process for hot metal as needed and then charged into a converter. Subsequently, molten steel tapped from the converter is subjected to secondary refining. In this secondary refining process, nitrogen concentration in the molten steel is adjusted by using the method for adjusting nitrogen concentration in molten steel according the present invention. Subsequently, steel is manufactured by performing continuous casting.

Example 1

Hereafter, the present invention will be described in detail in reference to examples.

Although the present invention will be described hereafter in detail in the case where a steel material is used as an analysis material, the present invention is not limited to the example described below at all.

Experimental Example 1 (Example of the Present Invention)

By using the apparatus for analyzing nitrogen 1 illustrated in FIG. 1, three steel standard samples and ten practical samples were analyzed. Among the ten practical samples, five of them were taken from steel ingots in which molten steel was subjected to argon gas bubbling before being solidified, and other five of them were taken from steel ingots in which molten steel was not subjected to argon gas bubbling before being solidified. Sample weight was about 1 g. Here, the argon gas feeding system 2 was prepared by fitting a flow rate regulator to a commercially available high-purity argon gas cylinder. The impulse furnace. 3, the dust filter 4, the oxidation column 6, and the column system 7 were configured by using necessary parts of nitrogen-oxygen analyzer EMGA-2200 (manufactured by HORIBA, Ltd.). As the discharge optical emission system 8, ozone generator ED-OG-R6 (manufactured by Ecodesign Inc.) was used. The photometrical analysis system 9 was configured by fitting ICCD (Intensified CCD) detector DH-520 (manufactured by Andor Technology Ltd.) to imaging spectrometer iHR320 (manufactured by HORIBA, Ltd.). The analytical wavelength of nitrogen gas used in the photometrical analysis system was 337 nm, and the nitrogen concentration of the sample was derived from the integral value of emission intensity corresponding to the wavelength.

Experimental Example 2 (Comparative Example 1)

The same 13 samples as those used in the experimental example 1 was analyzed by using the method (ammonia separation distillation-bispyrazolone spectrophotometric method) prescribed in appendix 2 of JIS G 1228 (2006). The reagents such as hydrochloric acid, sulfuric acid, sodium hydroxide, and so forth with the highest purity were used. By weighing out 4 g of each of the samples, by dissolving it with hydrochloric acid, by then performing specific treatments, and by then determining the absorption of light by using spectrophotometer 100-20 (manufactured by Hitachi, Ltd.), nitrogen concentration in the sample was derived.

Experimental Example 3 (Comparative Example 2)

The same ten practical samples as those used in experimental example 1 were analyzed by using the method (inert gas fusion thermal conductivity detection method) prescribed in appendix 5 of JIS G 1228 (2006). By weighing out 1 g of each of the samples, and by using helium gas as a carrier gas, analysis was performed by using nitrogen-oxygen analyzer EMGA-2200 (manufactured by HORIBA, Ltd.).

The experimental results are shown in Table 1

TABLE 1

| Experimental Number | Sample Name | Ar Bubbling | Experimental Example 1 | Experimental Example 2 | Experimental Example 3 |
|---|---|---|---|---|---|
| Standard Sample | GS-5a | — | 17 | 17 | 17 |
| " | GS-5c | — | 29 | 29 | 28 |
| " | GS-3b | — | 41 | 40 | 41 |
| Practical Sample | Practical Sample 1 | Undone | 45 | 46 | 44 |
| " | Practical Sample 2 | Undone | 39 | 40 | 38 |
| " | Practical Sample 3 | Undone | 35 | 34 | 36 |
| " | Practical Sample 4 | Undone | 42 | 42 | 41 |
| " | Practical Sample 5 | Undone | 47 | 47 | 46 |
| " | Practical Sample 6 | Done | 29 | 29 | 33 |
| " | Practical Sample 7 | Done | 33 | 32 | 36 |
| " | Practical Sample 8 | Done | 26 | 26 | 30 |
| " | Practical Sample 9 | Done | 24 | 23 | 27 |
| " | Practical Sample 10 | Done | 40 | 39 | 44 |
| | Time Required for Test | | 1 hour | 2 days | 1 hour |
| | Note | | Example of the Present Invention | Comparative Example | Comparative Example | unit: mass ppm

As shown in Table 1, the results of nitrogen analysis of experimental example 1 and experimental example 2 were almost the same for each of the all samples. However, although the results of nitrogen analysis of experimental example 3 were almost the same as those of experimental examples 1 and 2 for each of the standard samples and the practical samples 1 through 5, there were differences in the case of the practical samples 6 through 10.

The reason why there were difference for the practical samples in experimental example 3 is that the signal values determined by the thermal conductivity detector were increased, since there were bubbles of argon gas having a larger thermal conductivity than nitrogen gas in the samples.

On the other hand, in the case of experimental example 2, which involved a wet analysis method, and experimental analysis 1, which was the example of the present invention, since there was no negative effect of argon gas, the same results of nitrogen analysis were derived. That is, it is clarified that the present method for analysis is effective even for a metal sample including argon gas in the form of bubbles. However, in comparison in terms of testing time, while the analysis time was several minutes for each of the samples and about one hour in total in the case of the present method for analysis, the analysis time was two days in total in the case of experimental example 2, which involved a wet analysis method and many procedures in order to obtain the results. From the results described above, it is clarified that the method according to the present invention is a method for determining nitrogen concentration in metal accurately and rapidly.

Example 2

By using the same apparatus configurations and conditions as those used in experimental example 1, steel standard sample GS-3b (having a nitrogen concentration of 41 ppm) was repeatedly analyzed. Seven testing units were performed at intervals of several hours, where analysis was performed twice in a row in order to derive an average value in one unit. However, even when analysis was not performed, argon gas was flowed through the apparatus for analyzing nitrogen 1, and discharge was continued in the discharge optical emission system 8. Here, in the photometrical analysis system 9, by determining the emission intensities corresponding to the wavelength 357 nm of nitrogen gas and the wavelength 697 nm of argon gas, and by calculating the ratio of the former to the latter, nitrogen concentration was derived from the integral value of the calculated ratio.

Figure 5:
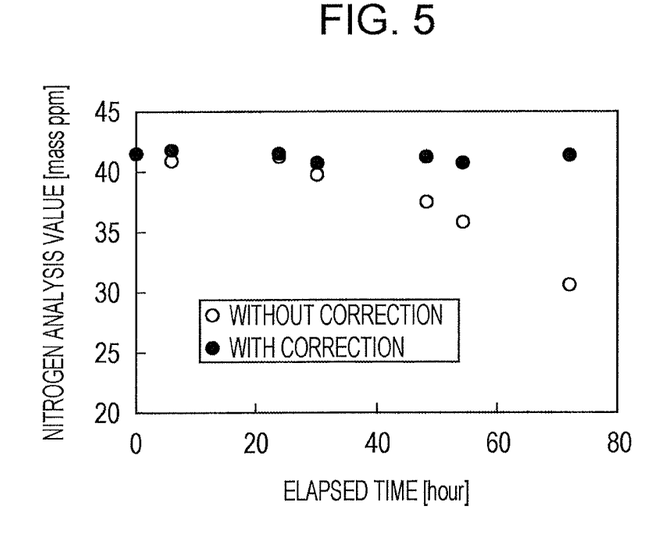
FIG. 5 is a diagram illustrating the uncorrected values and corrected values of nitrogen analysis results when a steel standard sample is analyzed at intervals of several hours during the apparatus for analyzing nitrogen in a metal sample according to the present invention is continuously operated for a long time.

The obtained results are illustrated in FIG. 5. As FIG. 5 indicates, it is clarified that, by determining the emission intensity of argon gas, and by performing correction on the basis of the emission intensity, it is possible to stably determine nitrogen content in a metal sample by correcting the error of analysis value due to the stain of a discharge tube.

Example 3

Figure 7:
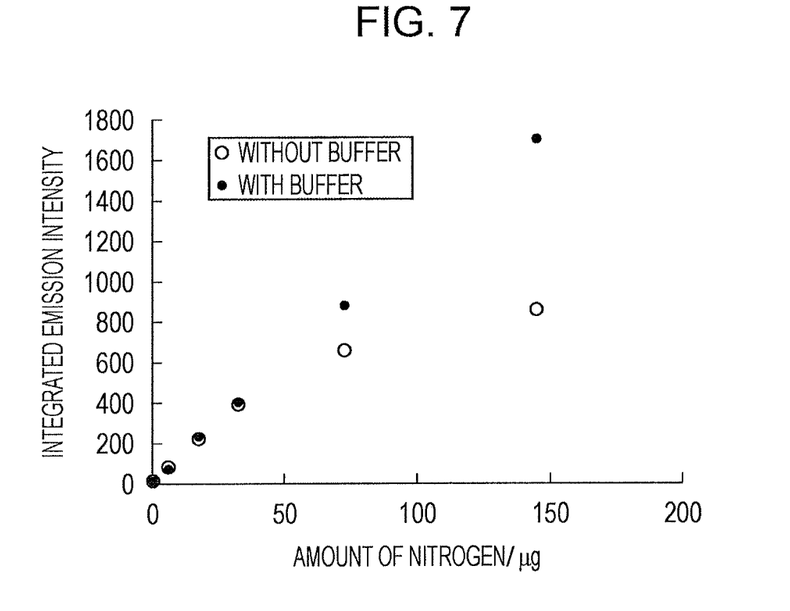
FIG. 7 is a diagram illustrating the relationship between integrated emission intensity and the amount of nitrogen in a steel sample (EXAMPLE 3).

By using the apparatus for analyzing nitrogen 30 illustrated in FIG. 6, and by using the same conditions as those used in experimental example 1, analysis was performed on steel standard sample JSS366-7 (having a nitrogen concentration of 6 ppm), steel standard sample GS-5a (having a nitrogen concentration of 17 ppm), steel standard sample GS-3c (having a nitrogen concentration of 32 ppm), and steel standard sample GS-2c (having a nitrogen concentration of 145 ppm) in the case where nitrogen-containing argon gas was passed through the buffer 40 (in the case where the buffer 40 was used) and in the case where nitrogen-containing argon gas was not passed through the buffer 40 (in the case where the buffer 40 was not used). Also, a blank test was performed. The weight of the samples other than GS-2c was 1 g, and the weights of the sample GS-2c were 0.5 g and 1 g. That is, a test was performed at six levels of nitrogen weight, that is, 0 μg, 6 μg, 17 μg, 32 μg, 72.5 μg, and 145 μg. The obtained relationship between integrated emission intensity and the amount of nitrogen in the steel sample is illustrated in FIG. 7. As FIG. 7 indicates, it is clarified that, while the emission intensity of nitrogen became saturated in a high-nitrogen region in the case where the buffer 40 was not used, emission intensity and the amount of nitrogen had a high-linearity correlation with each other even in a high-nitrogen region in the case where the buffer 40 was used.

Example 4

Example of the Present Invention

By using molten steel having a chemical composition containing 0.03 mass % to 0.06 mass % of carbon, 0.10 mass % or less of silicon, 0.3 mass % to 1.0 mass % of manganese, 0.050 mass % or less of phosphorus, and 0.005 mass % or less of sulfur, a nitrogen-concentration-adjusting test was performed with a target nitrogen concentration of 50 mass ppm.

By performing a pretreatment for hot metal involving a desulfurization treatment and a dephosphorization treatment on hot metal which had been tapped from a blast furnace, and by performing decarburization refining on the treated hot metal by using a converter, molten steel was prepared. When the molten steel was tapped from the converter into a ladle, deoxidation was performed by adding metallic aluminum to the molten steel, and metallic components were added. Subsequently, the obtained molten steel was transported to an RH vacuum degasser in order to perform vacuum degassing refining. In the RH vacuum degasser, by first circulating argon gas for a specified time under a high-vacuum condition, by then taking an analysis sample from the molten steel, and then by changing the circulation gas into a mixed gas of argon gas and nitrogen gas, a nitrogen-adding treatment was performed. By immediately cutting and polishing the sample taken from the molten steel, nitrogen analysis was performed. Nitrogen analysis was performed by using the apparatus for analyzing nitrogen according to the present invention illustrated in FIG. 1. By inputting the obtained nitrogen analysis value into a calculation equation in the RH degasser in order to reflect the analysis value in a nitrogen-adding treatment, a nitrogen-adding treatment was controlled with a target nitrogen concentration of 50 mass ppm.

Finally, by taking a sample from the molten steel which had been subjected to a nitrogen-adding treatment, and by determining nitrogen concentration by using the method (ammonium separation distillation-bispyrazolone spectrophotometric method) prescribed in appendix 2 of JIS G 1228 (2006), the determined value was compared with the target value. Such a treatment was performed 20 times.

Comparative Example

A sample taken before a nitrogen-adding treatment in an RH vacuum degasser was performed was analyzed by using the method (inert gas fusion thermal conductivity detection method) prescribed in appendix 5 of JIS G 1228 (2006). With the exception of this analysis method, the same procedures as those performed in the example of the present invention described above were performed. Such a treatment was performed 20 times.

The results obtained as described above are shown in Table 2.

TABLE 2

| Nitrogen Concentration after Refining | Example of the Present Invention | Comparative Example |
| --- | --- | --- |
| Average | 50.1 | 47.6 |
| Standard Deviation | 2.04 | 4.28 | unit: mass ppm

In the case of the example of the present invention, the average value of nitrogen analysis performed on the samples after a nitrogen-adding treatment in the RH vacuum degasser was performed was 50.1 mass ppm, which was almost equal to the target value, and the standard deviation was also satisfactory.

On the other hand, in the case of the comparative example where nitrogen analysis was performed by using an inert gas fusion thermal conductivity detection method, the average value was 47.6 mass ppm, which was lower than the target value, and a variation (standard deviation) was 4.28 mass ppm, which was relatively 2 times or more inferior than the standard deviation of the example of the present invention. This is considered to be because, since the taken sample of molten steel incidentally contained argon gas which was circulated immediately before the sampling, the analysis value obtained by using an inert gas fusion thermal conductivity detection method was higher than the practical nitrogen concentration, which resulted in the subsequent nitrogen-adding treatment being insufficiently performed.

REFERENCE SIGNS LIST 1, 20, 30 apparatus for analyzing nitrogen
2 argon gas feeding system
3 impulse furnace
4 dust filter
5 metal sample
6 oxidation column
7 column system
8 discharge optical emission system
9 photometrical analysis system
10 infrared absorption type carbon dioxide measuring device
21 argon gas feeding line
22 flow rate adjuster
31 graphite crucible
32 electrode
40 buffer
71 $CO_2$ remover
72 dehydrator
91 optical fiber
92 spectroscopic unit
93 photometric unit
94 operation unit

The invention claimed is:

1. A method for analyzing nitrogen in a metal sample containing a nitrogen component, the method comprising:
    performing impulse heating on the metal sample in an argon atmosphere to melt the metal sample and gasify the nitrogen component, and
    determining the amount of nitrogen gas present in the argon gas by using a gas discharge optical emission method.

2. The method for analyzing nitrogen in a metal sample according to claim 1, wherein the gas discharge optical emission method uses optical emission of the nitrogen gas at one or more of wavelengths 337 nm, 357 nm, 380 nm, and 406 nm.

3. The method for analyzing nitrogen in a metal sample according to claim 1, wherein,
    an emission intensity of nitrogen gas is corrected in accordance with an emission intensity of argon gas that is determined either at the same time as determining the emission intensity of the nitrogen gas, using the argon gas that contains the nitrogen gas, or using only flowing argon gas when not determining the emission intensity of the nitrogen gas.

4. The method for analyzing nitrogen in a metal sample according to claim 3, wherein,
optical emission of the argon gas at one or more of wavelengths 697 nm, 727 nm, 751 nm, 764 nm, 772 nm, 795 nm, 801 nm, 812 nm, and 826 nm is used.

5. An apparatus for analyzing nitrogen in a metal sample containing a nitrogen component, the apparatus comprising:
an impulse furnace in which the metal sample is melted in an argon gas atmosphere to gasify the nitrogen component;
an argon gas feeding system through which argon gas is fed into the impulse furnace;
a discharge optical emission system that induces the discharge optical emission of nitrogen gas generated in the impulse furnace and of argon gas in the impulse furnace by using a gas discharge optical emission method; and
a photometrical analysis system that determines the intensity of emission induced by the discharge optical emission system to determine nitrogen content in the metal sample.

6. The apparatus for analyzing nitrogen in a metal sample according to claim 5, wherein
the photometrical analysis system further includes a device that determines emission intensity of the argon gas.

7. The apparatus for analyzing nitrogen in a metal sample according to claim 5, the apparatus further comprising
a carbon dioxide measuring device of an infrared absorption type for determining carbon dioxide content between the impulse furnace and the discharge optical emission system.

8. The apparatus for analyzing nitrogen in a metal sample according to claim 5, the apparatus further comprising
a buffer for diluting the nitrogen in the argon gas between the impulse furnace and the discharge optical emission system.

9. The method for analyzing nitrogen in a metal sample according to claim 1, wherein,
when the nitrogen component is gasified by the impulse heating, the metal sample is heated to a temperature of 2500° C. or higher.

10. A method for adjusting nitrogen concentration in molten steel, the method comprising:
analyzing the nitrogen concentration of a sample of the molten steel by using the method for analyzing nitrogen in a metal sample according to claim 1; and
determining treatment conditions for adjusting nitrogen concentration on the basis of the nitrogen analysis value obtained through the analyzing.

11. A method for manufacturing steel, the method comprising
manufacturing steel by performing continuous casting on molten steel whose nitrogen concentration has been adjusted by using the method for adjusting nitrogen concentration in molten steel according to claim 10.

12. The method for analyzing nitrogen in a metal sample according to claim 2, wherein,
an emission intensity of nitrogen gas is corrected in accordance with an emission intensity of argon gas that is determined either at the same time as determining the emission intensity of the nitrogen gas, using the argon gas that contains the nitrogen gas, or using only flowing argon gas when not determining the emission intensity of the nitrogen gas.

13. The method for analyzing nitrogen in a metal sample according to claim 12, wherein,
optical emission of the argon gas at one or more of wavelengths 697 nm, 727 nm, 751 nm, 764 nm, 772 nm, 795 nm, 801 nm, 812 nm, and 826 nm is used.

14. The method for analyzing nitrogen in a metal sample according to claim 3, wherein,
when the nitrogen component is gasified by the impulse heating, the metal sample is heated to a temperature of 2500° C. or higher.

15. The apparatus for analyzing nitrogen in a metal sample according to claim 6, the apparatus further comprising
a carbon dioxide measuring device of an infrared absorption type for determining carbon dioxide content between the impulse furnace and the discharge optical emission system.

16. The apparatus for analyzing nitrogen in a metal sample according to claim 6, the apparatus further comprising
a buffer for diluting the nitrogen in the argon gas between the impulse furnace and the discharge optical emission system.

17. A method for adjusting nitrogen concentration in molten steel, the method comprising:
analyzing the nitrogen concentration of a sample of the molten steel by using the method for analyzing nitrogen in a metal sample according to claim 3; and
determining treatment conditions for adjusting nitrogen concentration on the basis of the nitrogen analysis value obtained through the analyzing.

18. A method for adjusting nitrogen concentration in molten steel, the method comprising:
analyzing the nitrogen concentration of a sample of the molten steel by using the method for analyzing nitrogen in a metal sample according to claim 9; and
determining treatment conditions for adjusting nitrogen concentration on the basis of the nitrogen analysis value obtained through the analyzing.

19. A method for manufacturing steel, the method comprising
manufacturing steel by performing continuous casting on molten steel whose nitrogen concentration has been adjusted by using the method for adjusting nitrogen concentration in molten steel according to claim 17.

20. A method for manufacturing steel, the method comprising
manufacturing steel by performing continuous casting on molten steel whose nitrogen concentration has been adjusted by using the method for adjusting nitrogen concentration in molten steel according to claim 18.

21. The method for analyzing nitrogen in a metal sample according to claim 1, wherein the step of performing impulse heating melts the metal sample entirely.

* * * * *